(12) United States Patent
Righini

(10) Patent No.: US 10,098,733 B2
(45) Date of Patent: Oct. 16, 2018

(54) EXPANDABLE PROSTHETIC VALVE HAVING ANCHORING APPENDAGES

(71) Applicant: Sorin Group Italia S.r.l., Milan (IT)

(72) Inventor: Giovanni Righini, Gland (CH)

(73) Assignee: Sorin Group Italia S.r.l., Milan (IT)

( * ) Notice: Subject to any disclaimer, the term of this patent is extended or adjusted under 35 U.S.C. 154(b) by 0 days.

(21) Appl. No.: 14/452,849

(22) Filed: Aug. 6, 2014

(65) Prior Publication Data

US 2014/0350666 A1 Nov. 27, 2014

Related U.S. Application Data

(63) Continuation of application No. 12/639,552, filed on Dec. 16, 2009, now Pat. No. 8,834,563.

(60) Provisional application No. 61/140,494, filed on Dec. 23, 2008.

(51) Int. Cl.
*A61F 2/24* (2006.01)

(52) U.S. Cl.
CPC .......... *A61F 2/2418* (2013.01); *A61F 2/2427* (2013.01); *A61F 2/2436* (2013.01); *A61F 2220/0058* (2013.01); *A61F 2220/0075* (2013.01); *A61F 2230/0054* (2013.01)

(58) Field of Classification Search
None
See application file for complete search history.

(56) References Cited

U.S. PATENT DOCUMENTS

| 3,143,742 A | 8/1964 | Cromie |
| 3,334,629 A | 8/1967 | Cohn |
| 3,363,442 A | 1/1968 | Kennedy et al. |
| 3,409,013 A | 11/1968 | Berry |
| 3,540,431 A | 11/1970 | Mobin-Uddin |
| 3,546,710 A | 12/1970 | Shumakov et al. |
| 3,574,865 A | 4/1971 | Hamaker |
| 3,587,115 A | 6/1971 | Shiley |
| 3,608,097 A | 9/1971 | Bellhouse et al. |
| 3,628,535 A | 12/1971 | Ostrowsky et al. |

(Continued)

FOREIGN PATENT DOCUMENTS

| CN | 101011298 A | 8/2007 |
| DE | 3640745 A1 | 6/1987 |

(Continued)

OTHER PUBLICATIONS

EP Communication issued in EP 07112385 dated Jul. 30, 2009.

(Continued)

*Primary Examiner* — Leslie Lopez

(74) *Attorney, Agent, or Firm* — Faegre Baker Daniels LLP

(57) ABSTRACT

A heart valve prosthesis includes an expandable prosthetic valve including three valve leaflets coupled to an anchoring structure. The anchoring structure includes an annular member and a plurality of arms movably coupled to the annular member at one end. The free ends of the arms extend radially away from the prosthesis toward a valve annulus. The arms are configured to fit in a space defined between an open native valve leaflet and a wall of a valve sinus. The arms are sufficiently resilient such that they resist downward movement in response to pressure exerted on the prosthesis, facilitating anchorage and stabilization of the prosthesis at the implantation site.

18 Claims, 4 Drawing Sheets

(56) References Cited

U.S. PATENT DOCUMENTS

| | | |
|---|---|---|
| 3,642,004 A | 2/1972 | Osthagen et al. |
| 3,657,744 A | 4/1972 | Ersek |
| 3,671,979 A | 6/1972 | Moulopoulos |
| 3,744,060 A | 7/1973 | Bellhouse et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,086,665 A | 5/1978 | Poirier |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,477,930 A | 10/1984 | Totten et al. |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,624,822 A | 11/1986 | Arru et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,692,164 A | 9/1987 | Dzemeshkevich et al. |
| 4,710,192 A | 12/1987 | Liotta et al. |
| 4,733,665 A | 3/1988 | Palmaz |
| 4,758,151 A | 7/1988 | Arru et al. |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,042,161 A | 8/1991 | Hodge |
| 5,047,041 A | 9/1991 | Samuels |
| 5,059,177 A | 10/1991 | Towne et al. |
| 5,061,273 A | 10/1991 | Yock |
| 5,084,151 A | 1/1992 | Vallana et al. |
| 5,085,635 A | 2/1992 | Cragg |
| 5,089,015 A | 2/1992 | Ross |
| 5,123,919 A | 6/1992 | Sauter et al. |
| 5,133,845 A | 7/1992 | Vallana et al. |
| 5,139,515 A | 8/1992 | Robicsek |
| 5,152,771 A | 10/1992 | Sabbaghian et al. |
| 5,161,547 A | 11/1992 | Tower |
| 5,163,953 A | 11/1992 | Vince |
| 5,163,954 A | 11/1992 | Curcio et al. |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,300,086 A | 4/1994 | Gory et al. |
| 5,314,468 A | 5/1994 | Ramos Martinez |
| 5,327,774 A | 7/1994 | Nguyen et al. |
| 5,332,402 A | 7/1994 | Teitelbaum |
| 5,350,398 A | 9/1994 | Pavcnik et al. |
| 5,360,014 A | 11/1994 | Sauter et al. |
| 5,370,684 A | 12/1994 | Vallana et al. |
| 5,370,685 A | 12/1994 | Stevens |
| 5,387,247 A | 2/1995 | Vallana et al. |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,423,886 A | 6/1995 | Arru et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,296 A | 2/1996 | Love et al. |
| 5,489,297 A | 2/1996 | Duran |
| 5,496,346 A | 3/1996 | Horzewski et al. |
| 5,505,689 A | 4/1996 | Kramer et al. |
| 5,507,767 A | 4/1996 | Maeda et al. |
| 5,522,884 A | 6/1996 | Wright |
| 5,545,209 A | 8/1996 | Roberts et al. |
| 5,545,211 A | 8/1996 | An et al. |
| 5,545,214 A | 8/1996 | Stevens |
| 5,545,215 A | 8/1996 | Duran |
| 5,554,185 A | 9/1996 | Block et al. |
| 5,560,487 A | 10/1996 | Starr |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,669,919 A | 9/1997 | Sanders et al. |
| 5,672,169 A | 9/1997 | Verbeek |
| 5,674,277 A | 10/1997 | Freitag |
| 5,693,066 A | 12/1997 | Rupp et al. |
| 5,695,498 A | 12/1997 | Tower |
| 5,698,307 A | 12/1997 | Levy |
| 5,702,368 A | 12/1997 | Stevens et al. |
| 5,712,953 A | 1/1998 | Langs |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,776,187 A | 7/1998 | Krueger et al. |
| 5,782,809 A | 7/1998 | Umeno et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,405 A | 9/1998 | Vanney et al. |
| 5,810,873 A | 9/1998 | Morales |
| 5,814,096 A | 9/1998 | Lam et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |

(56) References Cited

U.S. PATENT DOCUMENTS

| | | |
|---|---|---|
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,843,244 A | 12/1998 | Pelton et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,436 A | 3/1999 | Vanney et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,891,195 A | 4/1999 | Klostermeyer et al. |
| 5,906,619 A | 5/1999 | Olson et al. |
| 5,907,893 A | 6/1999 | Zadno Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,947,993 A | 9/1999 | Morales |
| 5,951,540 A | 9/1999 | Verbeek |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,972,016 A | 10/1999 | Morales |
| 5,980,570 A | 11/1999 | Simpson |
| 5,984,957 A | 11/1999 | Laptewicz, Jr. et al. |
| 5,997,573 A | 12/1999 | Quijano et al. |
| 6,010,531 A | 1/2000 | Donlon et al. |
| 6,019,739 A | 2/2000 | Rhee et al. |
| 6,019,790 A | 2/2000 | Holmberg et al. |
| 6,022,370 A | 2/2000 | Tower |
| 6,024,737 A | 2/2000 | Morales |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV et al. |
| 6,051,002 A | 4/2000 | Morales |
| 6,051,014 A | 4/2000 | Jang |
| 6,051,104 A | 4/2000 | Oriaran et al. |
| 6,059,809 A | 5/2000 | Amor et al. |
| 6,059,827 A | 5/2000 | Fenton, Jr. |
| 6,063,102 A | 5/2000 | Morales |
| 6,110,200 A | 8/2000 | Hinnenkamp |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,187,016 B1 | 2/2001 | Hedges et al. |
| 6,197,143 B1 | 3/2001 | Bodnar |
| 6,200,336 B1 | 3/2001 | Pavcnik et al. |
| 6,202,272 B1 | 3/2001 | Jackson |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,110 B1 | 8/2001 | Morales |
| 6,277,555 B1 | 8/2001 | Duran et al. |
| 6,287,339 B1 | 9/2001 | Vazquez |
| 6,299,637 B1 | 10/2001 | Shaolian et al. |
| 6,299,638 B1 | 10/2001 | Sauter |
| 6,302,906 B1 | 10/2001 | Goicoechea et al. |
| 6,309,382 B1 | 10/2001 | Garrison et al. |
| 6,309,383 B1 | 10/2001 | Campbell et al. |
| 6,309,417 B1 | 10/2001 | Spence et al. |
| 6,312,462 B1 | 11/2001 | McDermott et al. |
| 6,338,735 B1 | 1/2002 | Stevens |
| 6,348,063 B1 | 2/2002 | Yassour et al. |
| 6,350,277 B1 | 2/2002 | Kocur |
| 6,350,281 B1 | 2/2002 | Rhee |
| 6,352,547 B1 | 3/2002 | Brown et al. |
| 6,352,554 B2 | 3/2002 | De Paulis |
| 6,352,708 B1 | 3/2002 | Duran |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,387,117 B1 | 5/2002 | Arnold, Jr. et al. |
| 6,398,807 B1 | 6/2002 | Chouinard et al. |
| 6,402,780 B2 | 6/2002 | Williamson, IV et al. |
| 6,409,750 B1 | 6/2002 | Hyodoh et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,481,262 B2 | 11/2002 | Ching et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,506,201 B2 | 1/2003 | Di Caprio et al. |
| 6,508,833 B2 | 1/2003 | Pavcnik et al. |
| 6,510,722 B1 | 1/2003 | Ching et al. |
| 6,527,800 B1 | 3/2003 | McGuckin, Jr. et al. |
| 6,530,949 B2 | 3/2003 | Konya et al. |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,598,307 B2 | 7/2003 | Love et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,629,350 B2 | 10/2003 | Motsenbocker |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,692 B2 | 1/2004 | Rabkin et al. |
| 6,676,698 B2 | 1/2004 | McGuckin, Jr. et al. |
| 6,678,962 B1 | 1/2004 | Love et al. |
| 6,679,893 B1 | 1/2004 | Tran |
| 6,682,558 B2 | 1/2004 | Tu et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,716,241 B2 | 4/2004 | Wilder et al. |
| 6,719,789 B2 | 4/2004 | Cox |
| 6,726,713 B2 | 4/2004 | Schaldach, Jr. et al. |
| 6,730,118 B2 | 5/2004 | Spenser et al. |
| 6,730,377 B2 | 5/2004 | Wang |

(56) References Cited

U.S. PATENT DOCUMENTS

| | | |
|---|---|---|
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,161 B2 | 8/2004 | Brown et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,324 B2 | 1/2005 | Stobie |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,915,560 B2 | 7/2005 | Austin |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,966,924 B2 | 11/2005 | Holmberg |
| 6,968,607 B2 | 11/2005 | Motsenbocker |
| 6,974,474 B2 | 12/2005 | Pavcnik et al. |
| 6,974,476 B2 | 12/2005 | McGuckin, Jr. et al. |
| 6,981,982 B2 | 1/2006 | Armstrong et al. |
| 6,986,742 B2 | 1/2006 | Hart et al. |
| 6,988,881 B2 | 1/2006 | Motsenbocker et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,007,396 B2 | 3/2006 | Rudko et al. |
| 7,018,401 B1 | 3/2006 | Hyodoh et al. |
| 7,018,404 B2 | 3/2006 | Holmberg et al. |
| 7,018,406 B2 | 3/2006 | Seguin et al. |
| 7,021,114 B2 | 4/2006 | Perreault |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,069,794 B2 | 7/2006 | Motsenbocker et al. |
| 7,097,659 B2 | 8/2006 | Woolfson et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheimer et al. |
| 7,252,682 B2 | 8/2007 | Seguin |
| 7,255,706 B2 | 8/2007 | Rosengart |
| 7,258,698 B2 | 8/2007 | Lemmon |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,329,279 B2 | 2/2008 | Haug et al. |
| 7,335,218 B2 | 2/2008 | Wilson et al. |
| 7,338,484 B2 | 3/2008 | Schoon et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,357,814 B2 | 4/2008 | Gabbay |
| 7,367,984 B2 | 5/2008 | Kulcinski et al. |
| 7,374,571 B2 | 5/2008 | Pease et al. |
| 7,377,938 B2 | 5/2008 | Sarac et al. |
| 7,377,941 B2 | 5/2008 | Rhee et al. |
| 7,381,218 B2 | 6/2008 | Schreck |
| 7,384,411 B1 | 6/2008 | Condado |
| 7,393,360 B2 | 7/2008 | Spenser et al. |
| 7,427,291 B2 | 9/2008 | Liddicoat et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,455,690 B2 | 11/2008 | Cartledge et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,848 B2 | 9/2009 | Allen |
| 7,618,446 B2 | 11/2009 | Andersen et al. |
| 7,618,447 B2 | 11/2009 | Case et al. |
| 7,682,390 B2 | 3/2010 | Seguin |
| 7,708,775 B2 | 5/2010 | Rowe et al. |
| 7,780,726 B2 | 8/2010 | Seguin |
| 7,785,341 B2 | 8/2010 | Forster et al. |
| 7,806,919 B2 | 10/2010 | Bloom et al. |
| 7,857,845 B2 | 12/2010 | Stacchino et al. |
| 7,972,378 B2 | 7/2011 | Tabor et al. |
| 7,981,153 B2 | 7/2011 | Fogarty et al. |
| 8,006,535 B2 | 8/2011 | Righini et al. |
| 8,043,360 B2 | 10/2011 | McNamara et al. |
| 8,083,793 B2 | 12/2011 | Lane et al. |
| 8,109,996 B2 | 2/2012 | Stacchino et al. |
| 8,211,169 B2 | 7/2012 | Lane et al. |
| 8,535,373 B2 | 9/2013 | Stacchino et al. |
| 8,539,662 B2 | 9/2013 | Stacchino et al. |
| 8,540,768 B2 | 9/2013 | Stacchino et al. |
| 8,834,563 B2 | 9/2014 | Righini |
| 9,161,836 B2 | 10/2015 | Rolando et al. |
| 9,248,017 B2 | 2/2016 | Rolando et al. |
| 9,289,289 B2 | 3/2016 | Rolando et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0041928 A1 | 11/2001 | Pavcnik et al. |
| 2001/0044647 A1 | 11/2001 | Pinchuk et al. |
| 2001/0049558 A1 | 12/2001 | Liddicoat et al. |
| 2002/0010508 A1 | 1/2002 | Chobotov |
| 2002/0029014 A1 | 3/2002 | Jayaraman |
| 2002/0029783 A1 | 3/2002 | Stevens et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0103533 A1 | 8/2002 | Langberg et al. |

(56) References Cited

U.S. PATENT DOCUMENTS

| | | |
|---|---|---|
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0128702 A1 | 9/2002 | Menz et al. |
| 2002/0129820 A1 | 9/2002 | Ryan et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0161377 A1 | 10/2002 | Rabkin |
| 2002/0161392 A1 | 10/2002 | Dubrul |
| 2002/0161394 A1 | 10/2002 | Macoviak et al. |
| 2002/0183839 A1 | 12/2002 | Garrison et al. |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0114913 A1 | 6/2003 | Spenser et al. |
| 2003/0125795 A1 | 7/2003 | Pavcnik et al. |
| 2003/0125805 A1 | 7/2003 | Johnson et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191528 A1 | 10/2003 | Quijano |
| 2003/0192164 A1 | 10/2003 | Austin |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0073301 A1 | 4/2004 | Donlon et al. |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0123437 A1 | 7/2004 | Kokish |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson et al. |
| 2004/0167620 A1 | 8/2004 | Ortiz et al. |
| 2004/0186558 A1 | 9/2004 | Pavcnik et al. |
| 2004/0186563 A1 | 9/2004 | Lobbi |
| 2004/0193259 A1 | 9/2004 | Gabbay |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1* | 4/2005 | Nguyen ............ A61F 2/2418 623/1.26 |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |

(56) References Cited

U.S. PATENT DOCUMENTS

| | | |
|---|---|---|
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0166389 A1 | 8/2005 | Perreault et al. |
| 2005/0187616 A1 | 8/2005 | Realyvasquez |
| 2005/0197695 A1* | 9/2005 | Stacchino ............ A61F 2/2418 623/2.18 |
| 2005/0197696 A1 | 9/2005 | Gomez Duran |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0222675 A1 | 10/2005 | Sauter |
| 2005/0228495 A1 | 10/2005 | Macoviak |
| 2005/0229670 A1 | 10/2005 | Perreault |
| 2005/0234537 A1 | 10/2005 | Edin |
| 2005/0234546 A1 | 10/2005 | Nugent et al. |
| 2005/0240200 A1 | 10/2005 | Bergheim |
| 2005/0240256 A1 | 10/2005 | Austin |
| 2005/0240263 A1 | 10/2005 | Fogarty et al. |
| 2005/0261759 A1 | 11/2005 | Lambrecht et al. |
| 2005/0267529 A1 | 12/2005 | Crockett et al. |
| 2005/0283232 A1 | 12/2005 | Gabbay |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin et al. |
| 2006/0025855 A1 | 2/2006 | Lashinski et al. |
| 2006/0052867 A1 | 3/2006 | Revuelta et al. |
| 2006/0058775 A1 | 3/2006 | Stevens et al. |
| 2006/0058872 A1* | 3/2006 | Salahieh et al. ............ 623/2.18 |
| 2006/0074486 A1 | 4/2006 | Liddicoat et al. |
| 2006/0085060 A1 | 4/2006 | Campbell |
| 2006/0089711 A1 | 4/2006 | Dolan |
| 2006/0095117 A1 | 5/2006 | Popelar et al. |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1* | 8/2006 | Stacchino ............ A61F 2/2418 623/2.18 |
| 2006/0190017 A1 | 8/2006 | Cyr et al. |
| 2006/0195134 A1 | 8/2006 | Crittenden |
| 2006/0195184 A1 | 8/2006 | Lane et al. |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0253134 A1 | 11/2006 | Ortiz et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0265855 A1 | 11/2006 | Stenzel |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0027534 A1 | 2/2007 | Bergheim et al. |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0056346 A1 | 3/2007 | Spenser et al. |
| 2007/0061009 A1 | 3/2007 | Spenser et al. |
| 2007/0073387 A1 | 3/2007 | Forster et al. |
| 2007/0073392 A1 | 3/2007 | Heyninck Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100356 A1 | 5/2007 | Lucatero et al. |
| 2007/0100432 A1 | 5/2007 | Case et al. |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112415 A1 | 5/2007 | Bartlett |
| 2007/0112422 A1 | 5/2007 | Dehdashtian |
| 2007/0118209 A1 | 5/2007 | Strecker |
| 2007/0118215 A1 | 5/2007 | Moaddeb |
| 2007/0142968 A1 | 6/2007 | Prisco et al. |
| 2007/0162102 A1 | 7/2007 | Ryan et al. |
| 2007/0162113 A1 | 7/2007 | Sharkawy et al. |
| 2007/0168024 A1 | 7/2007 | Khairkhahan |
| 2007/0173861 A1 | 7/2007 | Strommer et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0237802 A1 | 10/2007 | McKay |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288000 A1 | 12/2007 | Bonan |
| 2007/0293942 A1 | 12/2007 | Mirzaee |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065011 A1 | 3/2008 | Marchand et al. |
| 2008/0065204 A1 | 3/2008 | Macoviak et al. |
| 2008/0065206 A1 | 3/2008 | Liddicoat |
| 2008/0071361 A1* | 3/2008 | Tuval ............... A61F 2/2418 623/2.1 |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |

(56) References Cited

U.S. PATENT DOCUMENTS

| | | |
|---|---|---|
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097595 A1 | 4/2008 | Gabbay |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1 | 10/2008 | Stacchino et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262593 A1 | 10/2008 | Ryan et al. |
| 2008/0262603 A1 | 10/2008 | Giaquinta et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0157175 A1 | 6/2009 | Benichou |
| 2009/0164004 A1 | 6/2009 | Cohn |
| 2009/0164006 A1 | 6/2009 | Seguin et al. |
| 2009/0171447 A1 | 7/2009 | Von Segesser et al. |
| 2009/0171456 A1 | 7/2009 | Kveen et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192602 A1 | 7/2009 | Kuehn |
| 2009/0192603 A1 | 7/2009 | Ryan |
| 2009/0198316 A1 | 8/2009 | Laske et al. |
| 2009/0209955 A1 | 8/2009 | Forster et al. |
| 2009/0210025 A1 | 8/2009 | Ameri |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0254165 A1 | 10/2009 | Tabor et al. |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0249661 A1 | 9/2010 | Righini et al. |
| 2010/0256723 A1 | 10/2010 | Murray |
| 2010/0262043 A1 | 10/2010 | Sauter et al. |
| 2010/0274351 A1 | 10/2010 | Rolando et al. |
| 2010/0292782 A1 | 11/2010 | Giannetti et al. |
| 2011/0082539 A1 | 4/2011 | Suri |
| 2011/0288636 A1 | 11/2011 | Rolando et al. |
| 2012/0172982 A1 | 7/2012 | Stacchino et al. |
| 2013/0172991 A1 | 7/2013 | Rolando et al. |
| 2013/0325112 A1 | 12/2013 | Stacchino et al. |
| 2013/0345800 A1 | 12/2013 | Stacchino et al. |
| 2014/0052243 A1 | 2/2014 | Rolando et al. |
| 2014/0052244 A1 | 2/2014 | Rolando et al. |
| 2015/0148895 A1 | 5/2015 | Stacchino et al. |

FOREIGN PATENT DOCUMENTS

| | | |
|---|---|---|
| DE | 19532846 A1 | 3/1997 |
| DE | 19546692 C2 | 6/1997 |
| DE | 29911694 U1 | 9/1999 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049815 A1 | 4/2002 |
| DE | 10121210 A1 | 11/2002 |
| DE | 10301026 A1 | 2/2004 |
| DE | 19857887 A1 | 5/2005 |
| DE | 102004019254 B3 | 11/2005 |
| EP | 0133420 B1 | 2/1988 |
| EP | 0155245 B1 | 5/1990 |
| EP | 0515324 B1 | 11/1992 |
| EP | 0401199 B1 | 1/1995 |
| EP | 0592410 B1 | 10/1995 |
| EP | 0850607 A1 | 7/1998 |
| EP | 1057460 A1 | 12/2000 |
| EP | 0778009 B1 | 7/2002 |
| EP | 1330213 B1 | 7/2003 |
| EP | 1259194 B1 | 2/2005 |
| EP | 1214020 B1 | 3/2005 |
| EP | 1353420 B1 | 3/2005 |
| EP | 1088529 B1 | 6/2005 |
| EP | 1014896 B1 | 11/2005 |
| EP | 1469797 A1 | 11/2005 |
| EP | 1603493 B1 | 12/2005 |
| EP | 1174098 B1 | 3/2006 |
| EP | 1600127 B1 | 11/2006 |
| EP | 1255510 A1 | 4/2007 |
| EP | 1143882 B1 | 12/2007 |
| EP | 1913901 A1 | 4/2008 |
| EP | 1690515 B1 | 7/2008 |
| EP | 1570809 B1 | 1/2009 |
| EP | 2047824 A1 | 4/2009 |
| EP | 2055266 A2 | 5/2009 |
| EP | 1370201 B1 | 9/2009 |
| EP | 2119417 A2 | 11/2009 |
| EP | 2133039 A2 | 12/2009 |
| EP | 2246011 A1 | 3/2010 |
| FR | 2788217 A1 | 7/2000 |
| FR | 2815844 A1 | 1/2003 |
| GB | 2083362 A | 3/1982 |
| GB | 2056023 A | 8/1983 |
| GB | 2433700 A | 12/2007 |
| JP | 11332997 A | 12/1999 |
| NL | 1017275 C2 | 8/2002 |
| SU | 1271508 A1 | 11/1986 |
| WO | WO1992009247 A1 | 6/1992 |
| WO | WO1995029640 A1 | 11/1995 |

(56) References Cited

FOREIGN PATENT DOCUMENTS

| | | |
|---|---|---|
| WO | WO1996039942 A1 | 12/1996 |
| WO | WO1997024989 A1 | 7/1997 |
| WO | WO1998014138 A1 | 4/1998 |
| WO | WO1998017202 A1 | 4/1998 |
| WO | WO1998029057 A1 | 7/1998 |
| WO | WO1999013802 A1 | 3/1999 |
| WO | WO1999053864 A1 | 10/1999 |
| WO | WO1999055255 A1 | 11/1999 |
| WO | WO1999056665 A1 | 11/1999 |
| WO | WO1999053866 A1 | 2/2000 |
| WO | WO2000006052 A1 | 2/2000 |
| WO | WO2000021464 A1 | 4/2000 |
| WO | WO2000030565 A1 | 6/2000 |
| WO | WO2000041652 A1 | 7/2000 |
| WO | WO2000044313 A1 | 8/2000 |
| WO | WO2000047136 A1 | 8/2000 |
| WO | WO2000047139 A1 | 8/2000 |
| WO | WO2000062714 A1 | 10/2000 |
| WO | WO2000062716 A1 | 10/2000 |
| WO | WO2001021076 A1 | 3/2001 |
| WO | WO2001021107 A1 | 3/2001 |
| WO | WO2001035870 A1 | 5/2001 |
| WO | WO2001049213 A2 | 7/2001 |
| WO | WO2001054625 A1 | 8/2001 |
| WO | WO2001062189 A1 | 8/2001 |
| WO | WO2001064137 A1 | 9/2001 |
| WO | WO2001076510 A2 | 10/2001 |
| WO | WO2002011646 A1 | 2/2002 |
| WO | WO2002022054 A1 | 3/2002 |
| WO | WO2002036048 A1 | 5/2002 |
| WO | WO2001021110 A2 | 8/2002 |
| WO | WO2002041789 A2 | 8/2002 |
| WO | WO2001021103 A2 | 10/2002 |
| WO | WO2002076348 A1 | 10/2002 |
| WO | WO2002092257 A1 | 11/2002 |
| WO | WO2002047575 A2 | 12/2002 |
| WO | WO2003011195 A2 | 2/2003 |
| WO | WO2003047468 A1 | 6/2003 |
| WO | WO2003003943 A2 | 11/2003 |
| WO | WO2003094797 A1 | 11/2003 |
| WO | WO2003003949 A2 | 1/2004 |
| WO | WO2004019825 A1 | 3/2004 |
| WO | WO2004082527 A2 | 9/2004 |
| WO | WO2004089250 A1 | 10/2004 |
| WO | WO2005004753 A1 | 1/2005 |
| WO | WO2004091455 A2 | 2/2005 |
| WO | WO2005046528 A1 | 5/2005 |
| WO | WO2005062980 A2 | 7/2005 |
| WO | WO2005082578 A1 | 9/2005 |
| WO | WO2006005015 A2 | 1/2006 |
| WO | WO2006026371 A1 | 3/2006 |
| WO | WO2006044679 A1 | 4/2006 |
| WO | WO2006086135 A2 | 8/2006 |
| WO | WO2006088712 A1 | 8/2006 |
| WO | WO2006093795 A1 | 9/2006 |
| WO | WO2006117016 A1 | 11/2006 |
| WO | WO2006124649 A2 | 11/2006 |
| WO | WO2006127089 A1 | 11/2006 |
| WO | WO2006127765 A1 | 11/2006 |
| WO | WO2006135831 A1 | 12/2006 |
| WO | WO2006136930 A1 | 12/2006 |
| WO | WO2007009117 A1 | 1/2007 |
| WO | WO2007053243 A2 | 5/2007 |
| WO | WO2007030825 A2 | 6/2007 |
| WO | WO2007071436 A2 | 6/2007 |
| WO | WO2007130537 A1 | 11/2007 |
| WO | WO2006007401 A2 | 1/2008 |
| WO | WO2001021097 A2 | 3/2008 |
| WO | WO2008028569 A1 | 3/2008 |
| WO | WO2008035337 A2 | 3/2008 |
| WO | WO2008047354 A2 | 4/2008 |
| WO | WO2008070797 A2 | 6/2008 |
| WO | WO2008089365 A2 | 7/2008 |
| WO | WO2008138584 A1 | 11/2008 |
| WO | WO2008150529 A1 | 12/2008 |
| WO | WO2009002548 A1 | 12/2008 |
| WO | WO2009024716 A2 | 2/2009 |
| WO | WO2009029199 A1 | 3/2009 |
| WO | WO2009042196 A2 | 4/2009 |
| WO | WO2009045331 A1 | 4/2009 |
| WO | WO2009045338 A1 | 4/2009 |
| WO | WO2009061389 A2 | 5/2009 |
| WO | WO2009091509 A1 | 7/2009 |
| WO | WO2009094188 A2 | 7/2009 |
| WO | WO2009111241 A2 | 9/2009 |

OTHER PUBLICATIONS

Extended European Search Report issued in EP 07106697, dated Aug. 21, 2007, 6 pages.
Extended European Search Report issued in EP 07112385, dated Apr. 1, 2008, 11 pages.
Extended European Search Report issued in EP 10168449, dated Aug. 19, 2010, 3 pages.
International Search Report and Written Opinion issued in PCT/US2010/028873, dated Jun. 15. 2010, 11 pages.
Partial European Search Report issued in EP 07112385, dated Jan. 4, 2008, 5 pages.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. I 664-669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004.
Boudjemline, et al., "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-116.
Boudjemline, et al, "Percutaneous Implantation of a Valve in the Descending Aorta in Lambs," European Heart Journal (England), Jul. 2002, pp. 1045-1049.

(56) References Cited

OTHER PUBLICATIONS

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Decision Rejecting Opposition dated Oct. 19, 2011, filed in EP Patent 1690515, 22 pages.
Definition of Hinge downloaded from Voculabulary.com, received at the EPO on Dec. 18, 2012, 1 page.
Definition of Hinge, downloaded from www.meriam-webster.com on Jan. 31, 2013, 3 pages.
Definition of Minimum, dovvnloaded from www.meriam-webster.com on Jan. 31, 2013, 2 pages.
European Search Report issued in EP 10183557, dated Apr. 11, 2011, 7 pages.
European Search Report issued in EP App No. 08165227, dated Mar. 13, 2009.
European Search Report issued in EP Application No. 05004289, dated Jun. 2, 2005, 3 pages.
European Search Report issued in EP Application No. 06101425, dated May 3, 2006, 6 pages.
European Search Report issued in EP Application No. 08150075, dated Mar. 27, 2008, 6 pages.
European Search Report issued in EP Application No. 11425029, dated Aug. 17, 2011, 5 pages.
European Search Report issued in EP Application No. 11425030, dated Aug. 10, 2011, 5 pages.
Search Report issued in EP Publication No. 1570809 (EP App No. 05004289,4), dated Jan. 5, 2007, 5 pages.
Extended European Search Report issued in EP 09179414, dated Oct. 18, 2010, 8 pages.
Extended European Search Report issued in EP Application 09158822, dated Sep. 29, 2009, 5 pages.
Grube, Eberhard et al., Case Report entitled "First Report on a Human Percutaneous Translurninal Implantation of a Self-Expanding Valve Prosthesis for Interventional Treatment of Aortic Valve Stenosis", Valvular Heart Disease, Catheterization and Cardiovascular Interventions, 2005, 66:465-469.
Hanzel, et al., "Complications of percutaneous aortic valve replacement: experience with the CriberEdwardsTm percutaneous heart valve," EuroIntervention Supplements (2006), I (Supplement A) A3-A8.
Huber, et al., "Do Valved Stents Compromise Coronary Flow?" Eur. J. Cardiothorac. Surg. 2004;25:754-759.
International Search Report and Written Opinion issued in PCT/IB2012/050608, dated Jul. 24, 2012, 9 pages.
International Search Report issued in International Application No. PCT/I B2006/000967, published as WO2006/085225, dated Jul. 6, 2006.
Khambadkone, "Nonsurgical Pulmonary Valve Replacement: Why, When, and How?" Catheterization and Cardiovascular Interventions—Official journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for oft-pump mitral valve replacement," European Journal of Cardio Thoracic Surgery, 28:194-198, 2005.
Medtech Insight, "New Frontiers in Heart Valve Disease," vol. 7, No. 8 (2005).
Minutes of the Oral Proceedings dated Oct. 19, 2011, filed in EP Patent 1690515, 4 pages.
Notice of Appeal dated Dec. 28, 2011 flied in EP Patent 1690515, 3 pages.
Notice of Opposition with Facts, Evidence and Arguments filed in EP Patent 1690515 dated Apr. 30, 2009, 21 pages.
Palacios, "Percutaneous Valve Replacement and Repair, Fiction or Reality?" Journal of American College of Cardiology, vol. 44, No. 8 (2004) pp. 1662-1663.
Pavcnik et al., "Aortic and venous valve for percutaneous insertion," Min. Invas, Ther. & Allied Techol. 2000, vol. 9, pas, 287-292.
Pelton et al., "Medical Uses of Nitinol," Materials Science Forum vols. 327-328, pp. 63-70 (2000).
Response dated Dec. 9, 2009 to the Notice of Opposition filed in EP Patent 1690515 by ATS Medical Inc., 25 pages.
Response dated Mar. 23, 2011 to Summons dated Sep. 16, 2010, filed in EP Patent 1690515, 21 pages.
Response dated Sep. 17, 2012 to Grounds for Appeal dated Feb. 29, 2012, filed in EP Patent 1690515, 48 pages.
Response dated Sep. 17, 2012, Attachment A.
Response dated Sep. 17, 2012, Attachment B.
Roth, Mark, "Old metal heart valve did its job for 42 years", Pittsburgh Post-Gazette, Wednesday Mar. 5, 2008, 3 pages.
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Stassano et al., "Mid-term results of the valve-on-valve technique for bioprosthetic failure," Eur. J. Cardiothorac. Surg. 2000; 18:453-457.
Statement of Grounds for Appeal dated Feb. 29, 2012, filed in EP Patent 1690515, 41 pages.
Summons dated Apr. 15, 2013 with Facts and Submissions to Date to Attend Oral Proceedings on Nov. 5, 2013, filed in EP Patent 1690515, 13 pages.
Summons dated Sep. 16, 2010 with Facts and Submissions to Date, filed in EP Patent 1690515, 20 pages.
Webb, et al., "Percutaneous Aortic Valve Implantation Retrograde from the Femoral Artery," Circulation (2006), 1 13;842-850.
International Search Report and Written Opinion issued in PCT/IB2012/050604, dated Jul. 26, 2012, 9 pages.
European Search Report issued in EP Application No. 11425310, dated May 31, 2012, 8 pages.
Grube, Eberhard, et al. Percutaneous Implantation of the Core Valve Self-Expanding Valve Prosthesis in High-Risk Patients With Aortic Valve Disease: The Siegburg First-in-Man Study. American Heart Association, Circulation, 114:1616-1624, 2006.

* cited by examiner

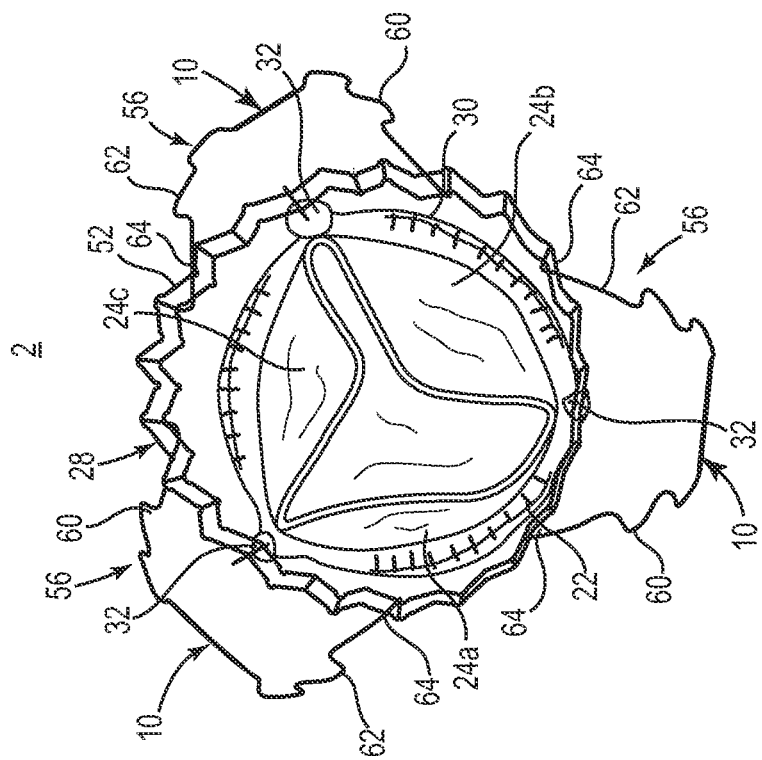
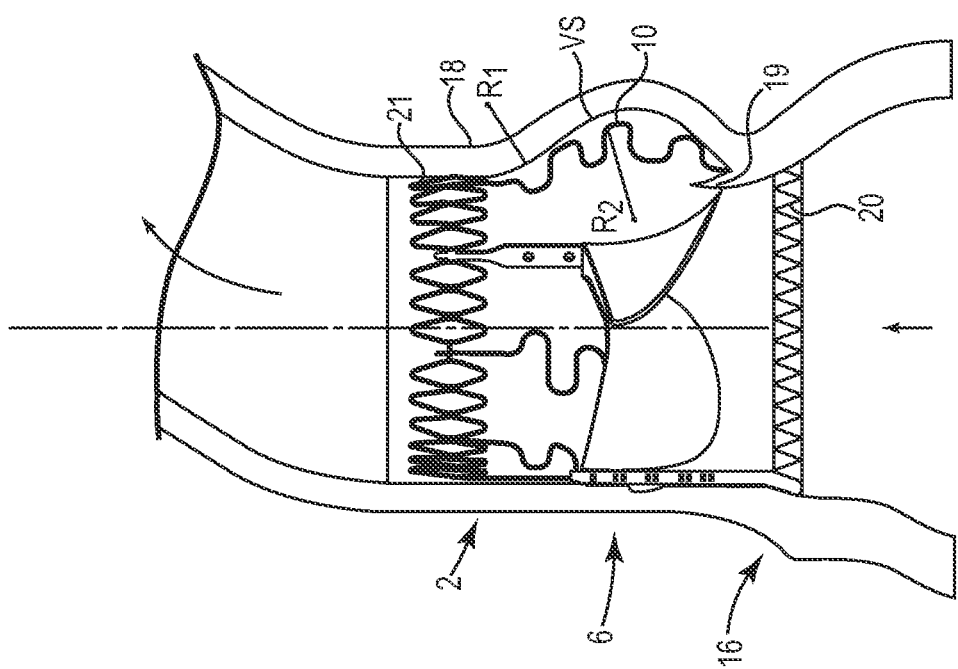

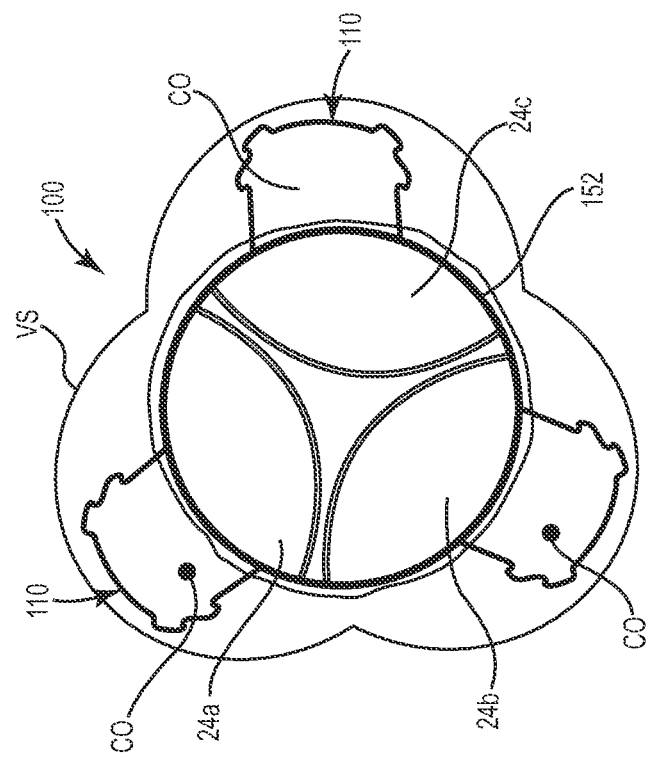
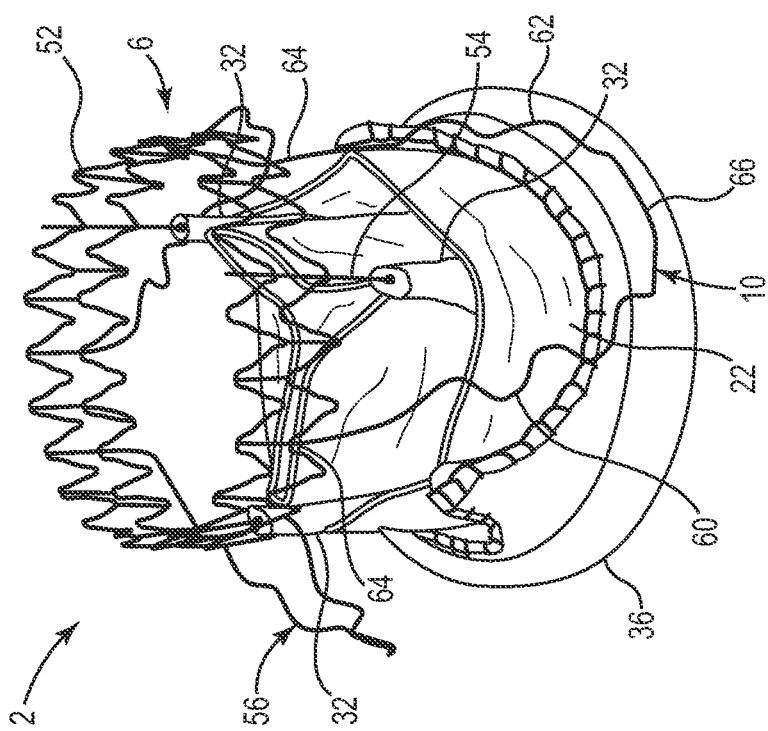
Fig. 4
Fig. 3

EXPANDABLE PROSTHETIC VALVE HAVING ANCHORING APPENDAGES

CROSS-REFERENCE TO RELATED APPLICATION

This application is a continuation of U.S. application Ser. No. 12/639,552, filed Dec. 16, 2009, which claims the benefit of Provisional Application No. 61/140,494, filed Dec. 23, 2008, entitled "Expandable Prosthetic Valve Having Anchoring Appendages," which is herein incorporated by reference in its entirety.

BACKGROUND

The present invention relates to cardiac-valve prostheses. More specifically, the present invention is directed to a prosthesis amenable to a minimally-invasive implantation procedure having a stent-like anchoring structure. These prostheses (often referred to as percutaneous valves) typically include an anchoring structure, which is able to support and fix the valve prosthesis at the implantation site, and prosthetic valve elements, generally in the form of leaflets or flaps, which are connected to the anchoring structure and configured to regulate blood flow. The prosthetic valve may be introduced into a position corresponding to the natural annulus and deployed in situ by divaricating the native valve leaflets (or following removal of the native leaflets).

SUMMARY

The present invention, according to one exemplary embodiment, is a valve prosthesis for implantation in or near a human heart at a valve site including one or more valve sinuses. The prosthesis includes an anchoring structure comprising an annular outflow member, an annular inflow member, and a plurality of arms each coupled at one end to the annular outflow member, the arms having a first end coupled to the annular outflow member and a second end configured to contact a base of the valve sinus. It further includes a plurality of leaflets coupled to the anchoring structure and adapted to substantially allow blood flow in a first direction and to substantially prevent blood flow in a second direction. The annular outflow member has an expanded position generally configured to engage a vessel wall at a location distal to the valve sinus, and at least one of the plurality of arms is shaped to engage substantially an entire longitudinally extending surface of the valve sinus.

According to another embodiment, the present invention is a valve prosthesis having an plurality of valve leaflets coupled to an anchoring structure. The anchoring structure includes one or more anchoring arms adapted to substantially engage a valve sinus. The anchoring arms include a free end adapted to contact a base of the valve sinus adjacent one or more native valve leaflets.

The present invention, according to yet another embodiment, is a method of implanting an expandable valve prosthesis at a target implantation site in or near a patient's heart, the implantation site including at least one valve sinus. The method includes providing a heart valve prosthesis including a prosthetic valve having three leaflets coupled to an anchoring structure, the anchoring structure including an annular member coupled to a plurality of arms having first and second ends, such that the second ends are not directly coupled to the anchoring structure; transitioning the prosthesis from an expanded position to a collapsed position; delivering the prosthesis to a target implantation site within a patient's heart in a minimally invasive manner; facilitating expansion of the prosthesis including the arms; and positioning the second ends of the arms in a space defined between a native valve leaflet and a sinus wall.

According to a further embodiment, the present invention is a kit for implanting a heart valve prosthesis at an implantation site within a patient's heart. The kit includes an expandable heart valve prosthesis including an expandable prosthetic heart valve having three leaflets coupled to an anchoring structure, the anchoring structure including an annular outflow member and a plurality of arms movably coupled to the annular member, wherein the arms are configured to contact a base of a valve sinus adjacent an open native heart valve leaflet; a crimping tool adapted to transition the prosthesis from an expanded position to a collapsed position; and a delivery catheter adapted to deliver the prosthesis to the implantation site.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 is a sectional view of an aorta of the human heart having an implanted expandable heart valve prosthesis according to an embodiment of the present invention implanted within or adjacent to an aortic valve.

FIG. 2 is a top perspective view of an expandable prosthetic valve including an anchoring structure according to an embodiment of the present invention.

FIG. 3 is a perspective view of an expandable prosthetic valve including an anchoring structure according to another embodiment of the present invention.

FIG. 4 is a top, schematic view of an expandable prosthetic valve implanted at an implantation site according to an embodiment of the present invention.

Figure 5:
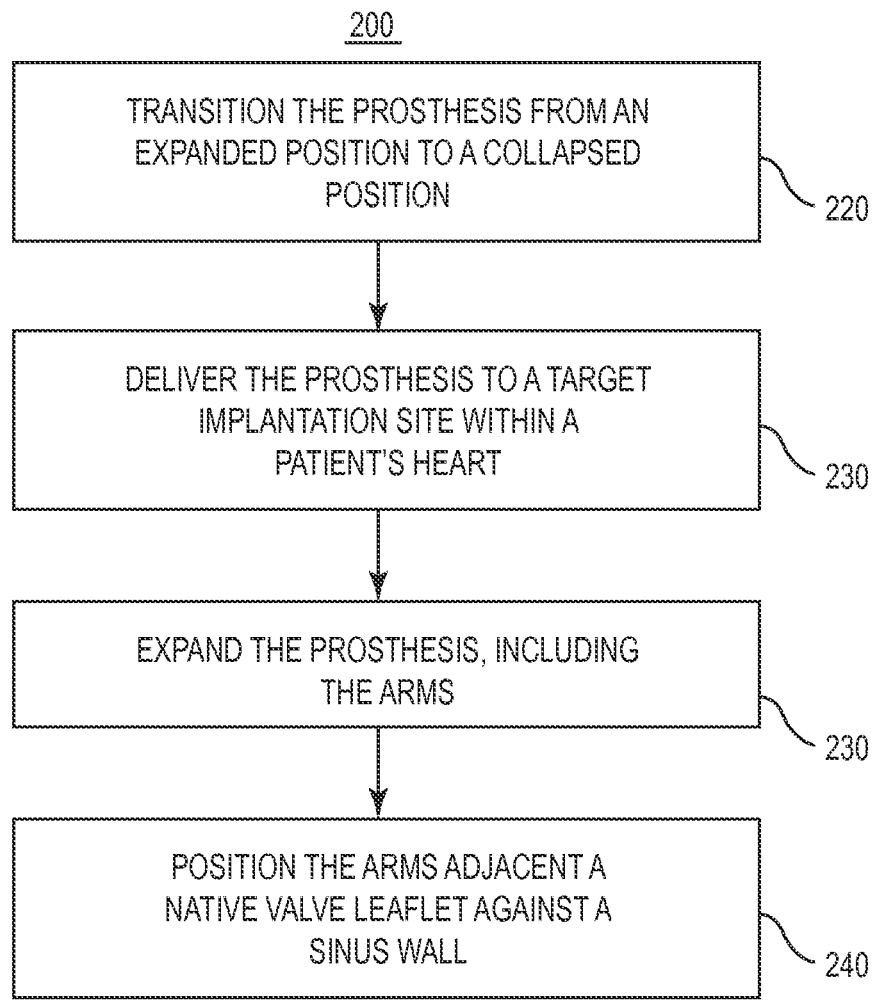
FIG. 5 is a flow chart of a method of implanting an expandable prosthetic heart valve according to various embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a perspective view of an expandable prosthetic valve 2, according to an embodiment of the present invention. As shown in FIG. 1, the prosthetic valve 2 includes an anchoring structure 6 having anchoring arms or appendages 10. The prosthetic valve 2 is shown implanted within or adjacent an aortic annulus 16 of an ascending aorta 18, which is coupled to the left ventricle of a heart. During normal operation, the left ventricle pumps blood out of the heart through the aortic annulus 16 and into the ascending aorta 18 (as indicated by the arrows in FIG. 1). The prosthetic heart valve 2 is suitable for implantation within or adjacent a valved intraluminal site using endovascular delivery techniques known to those of skill in the art. Such a site includes, for example, the aortic valve 16 (as shown in FIG. 1), the tricuspid valve, the pulmonary valve, and the mitral valve of a patient's heart. The prosthetic heart valve 2 is implanted within the valved intraluminal site such that the native valve leaflets 19 are held in the open position and the prosthetic heart valve 2 is expanded to bear against a vessel or sinus wall, e.g., the Valsalva sinus (VS). The prosthetic valve 2, includes an annular proximal (or inflow) ring 20 located at or near the native valve annulus and an annular distal (or outflow) ring 21 generally located at an opposite end of the valve (i.e., away from the valve annulus).

FIG. 2 is a top perspective view of a prosthetic valve and FIG. 3 is a side perspective view of a prosthetic valve according to various embodiments of the present invention. As shown in FIGS. 2 and 3, each of the expandable prosthetic valves 2 includes a valve sleeve 22 including three leaflets 24*a*, 24*b*, and 24*c* coupled to the anchoring structure 6. The valve sleeve 22 may be constructed according to various techniques known in the art. The valve sleeve 22 includes a base portion 30 with an overall annular pattern, designed to extend from the lower portion of the prosthetic valve 2, which at the implantation site, is in a position proximal to the valve annulus. Three pleat formations 32 extend distally from the base portion 30. The valve leaflets 24*a*, 24*b* and 24*c* extend between adjacent pleat formations 32. Each valve leaflet 24*a*, 24*b* and 24*c* has a proximal edge with an arched pattern that extends from the base formation 30 and along two adjacent pleat formations 32, and a distal edge that extends towards a central orifice of the prosthesis, so as to cooperate with the edges of the other valve leaflets in a coapting fashion.

As is generally known by those of ordinary skill in the art, in operation, as blood flows out of the ventricle and through the prosthetic valve 2, the compliant valve leaflets 24*a*, 24*b*, 24*c* are adapted to deform and move towards the support structure 6 to allow free flow of the blood through the prosthesis. When the pressure gradient, and hence the direction of flow, of the blood through the prosthesis is reversed (i.e., blood is flowing into the left ventricle), the coapting edges of the valve leaflets 24*a*, 24*b*, 24*c* move towards each other (e.g., contact each other) such that the leaflets substantially close and thus prevent the flow of the blood through the prosthesis 2. In some embodiments of the present invention, the valve leaflets 24*a*, 24*b*, 24*c* are made in such a way as to assume, in the absence of external stresses, the closed configuration. In various embodiments, as shown in FIG. 3 the valve sleeve 22 includes an annular securing device 36, located at or near a proximal end of the valve, for securing the prosthetic valve 2 to the valve annulus. According to some embodiments, the annular securing device 36 is a sewing ring such as that shown and described in U.S. Pat. No. 5,163,954, which is hereby incorporated by reference.

The anchoring structure 6 is adapted to stabilize and secure the prosthetic valve 2 at an implantation site within a patient's body. As shown in FIG. 3, the anchoring structure 6 includes an annular outflow member 52, a plurality of vertical support members 54, and at least three anchoring appendages or arms 10 coupled to the annular member 52 and adapted to extend radially outward from the support structure 6. In some embodiments, the arms 10 are movably coupled to the support structure such that they can transition from a collapsed position to an extended position. The annular member 52 and the respective arms 10, together with an annular inflow ring 20 facilitate anchoring of the prosthetic valve 2 at the desired implantation site. According to some embodiments, the annular inflow ring 20 is dimensioned to secure the valve prosthesis against a proximal surface of the valve annulus. According to some embodiments, the prosthetic valve 2 includes a seal located at or near the proximal end to prevent perivalvular leakage. Such a seal is disclosed, for example, in co-pending, commonly assigned U.S. patent application Ser. No. 11/871,447, filed Oct. 12, 2007, entitled "Expandable Valve Prosthesis With Sealing Mechanism," which is hereby incorporated by reference.

In some embodiments, as discussed in further detail below, the anchoring structure 6 can include a plurality of anchoring arms 10 made at least partially of shape-memory material (e.g., Nitinol), which enable regulation of the anchoring and support through the control of the memory of the shape-memory material (e.g., by controlling its temperature). According to other embodiments, the entire anchoring structure 6 is made from a shape memory material. In still other embodiments, the anchoring structure 6 can be made of a re-absorbable material, whereas the valve sleeve 22 can be constituted by biological and/or synthetic tissues, which are in part colonizable or re-absorbable.

During implantation, the prosthetic valve 2 is advanced towards the implantation site in a radially contracted configuration, with the annular member 52 in a radially collapsed configuration. According to some embodiments, the annular member 52 has a collapsed diameter of about 5 to about 15 mm in the collapsed configuration. Upon delivery to the target implantation site, expansion of the annular member 52 is facilitated until it reaches an expanded configuration. According to some embodiments, the diameter of the annular member 52 ranges from about 18 mm to about 30 mm in the expanded configuration.

According to some embodiments, the annular member 52 has an open mesh structure similar to the structure of a stent used for angioplasty. The mesh structure facilitates expansion of the annular member 52 from a collapsed configuration to an expanded configuration similar to the movement of expansion in situ of an angioplasty stent. According to some embodiments, the annular member 52 has a rhomboidal-mesh structure. In other embodiments, the annular member 52 can be fabricated to have any mesh structure configured to radially expand and collapse in the manner described above.

According to some embodiments, the annular member 52 is at least slightly flared outward like an enlarged opening of the flow duct of the blood. This configuration may facilitate positive anchorage of the annular member 52 at the implantation site. In other embodiments, the annular member 52 flares or curves inwardly, such as is described for example in commonly assigned, co-pending U.S. Publication No. 2009/0287296, filed May 13, 2009, entitled "Atraumatic Prosthetic Heart Valve Prosthesis," which is hereby incorporated by reference. Securely anchoring the prosthetic valve 2 at the implantation site promotes perivalvar tightness, improving the hemodynamics and adapting the lines of blood flow in the ventricular chamber to the flow tube constituted by the valve sleeve.

As best shown in FIG. 3, a plurality of vertical support members 54 are coupled at their proximal ends to the annular member 52. The vertical support members 54 are configured to support the valve sleeve 22 on the anchoring structure 6. According to some embodiments, the support members 54 include generally flat bars set at an angular distance apart from one another by about 120°. In some embodiments, each of the generally flat bars forming the support member 54 include a plurality of apertures or holes formed therein. As shown in FIG. 3, each of the pleat formations 32 embraces one of the support members 54, with the valve leaflets 24a, 24b and 24c extending in a festoon between two adjacent support members 54. The generally apertured structure of the support members 54 enables the valve sleeve 22 to be secured to the support structure 6 by, for example, suturing stitches according to techniques known to those of skill in the art. In the case where flaps of polymeric materials are used, the flaps can be formed directly on the structure, using techniques such as, for example, dip casting.

Also coupled to the annular member 52 are a plurality of anchoring arms 10. As shown in FIGS. 1-4, each of the arms 10 includes first and second legs 60, 62 each having a proximal end 64 and a generally U-shaped portion 66 coupled to and bridging between the first and second legs 60, 62. The arms 10, in one embodiment, are coupled to the annular member 52 such that they are disposed over (e.g., centered with respect to) each of the support members 54. As shown in FIG. 1, according to various embodiments, the prosthetic valve 2 is sized and shaped such that the annular member 52 is located at or near a distal-most portion of the valve. In this embodiment, the prosthetic valve 2 has a length such that once implanted at an appropriate site, the annular member 52 is positioned distal to the valve sinus (VS), while the annular inflow member 20 is located at or near the native valve annulus 16. According to various embodiments, the anchoring arms 10 extend radially outward a sufficient distance to allow a native, stenotic valve leaflet to fit between the arm 10 and the corresponding portion of the body of the anchoring structure 6. As shown, the arms 10 also extend from the outflow ring 21 at the distal end of the valve towards the inflow ring 20 at the proximal end of the valve.

Additionally, according to some embodiments, each of the arms 10 is movably coupled to the annular member 52 such that they are able to transition from a collapsed position suitable for implantation to an extended position. In the extended position, the arms 10 are configured to anchor and secure the prosthesis at an implantation site. In some embodiments, as shown for example in FIG. 1, the arms 10 extend proximally a sufficient length to engage the base of the valve sinus (VS), generally at or near the intersection of the valve sinus and the native valve leaflets 19. In this configuration, any force applied to the distal end of the prosthetic valve 2 is transferred by the arms 10 to the base of the valve sinus. The arms 10, thus operate to generally secure the prosthetic valve 2 at the implantation site adjacent the valve annulus and prevent undesired movement or migration of the valve.

According to some embodiments, as shown in FIG. 3, the first and second legs 60, 62 of each arm 10 are made in the form of struts that extend in a generally sinusoidal fashion, with bends or open loops situated on either side with respect to an imaginary line extending approximately in the direction of the overall cylindrical shape of the prosthesis 2. In other embodiments, the sinusoidal pattern can be obtained with bends or open loops that extend from one side and from the other with respect to a line that extends in a circumferential direction with respect to the prosthesis. In another embodiment, the first and second legs may have a mesh structure extending there between. According to some embodiments, the legs 60 include a bends or loops angled away from corresponding bends or loops on the legs 62, to provide additional anchoring within the Valsalva sinus. The bends or loops, for example, may include a curvature adapted to generally match the corresponding portion of the interior wall of the Valsalva sinus. While the embodiments shown in FIGS. 2-4 have three arms 10, the present invention contemplates embodiments having more or fewer arms 10. In one embodiment, for example, the anchoring structure 6 includes six arms 10, two arms associated with each of the three Valsalva sinuses.

The U-shaped portion 66 extends between and bridges the first and second legs 60, 62 of each arm 10. According to some embodiments, the U-shaped portion 66 is integrally formed with each of the legs 60, 62. According to other embodiments, the U-shaped portion 66 is a separate piece welded to or otherwise attached to each of the legs 60, 62 such that it extends between and forms a bridge between each of the legs 60, 62. According to some embodiments, the length of the U-shaped portion 66 is selected such that the legs 60, 62 are configured to press against and inwardly angled surface of the inner wall of the Valsalva sinus, such that anchoring is improved.

The U-shaped portion 66 may be substantially straight, arched, or otherwise bent at the portion extending between the first and second legs 60, 62. The U-shaped portion 66 is generally smooth and free from rough edges such that when it contacts and presses up against tissue at the implantation site it will not cause trauma at the site. According to some embodiments, the U-shaped portion 66 has a curved shape configured to generally match the contours of the base of the valve sinus. Additionally, the U-shaped portion 66 may include a sleeve or other protective coating. The sleeve or protective coating may be formed from a biocompatible polymer or polymeric coating. According to further embodiments the sleeve or protective coating may include a therapeutic agent, such as a steroid, to reduce inflammation at the implantation site.

According to some embodiments, as shown for example in FIG. 1, the anchoring arms 10 have an arched or curved configuration, such that the arms 10 generally follow the longitudinal contours of the patient's valve sinus wall (i.e., from the start of the valve sinus near the valve annulus extending distally away from the valve annulus to the end of the sinus at the vessel wall). In these embodiments, the anchoring arms 10 substantially conform to or engage the sinus walls so as to ensure firm anchorage in situ of the prosthetic valve 2. Examples of arms or support struts configured to substantially engage the sinus walls are shown in co-pending, commonly assigned U.S. patent application Ser. No. 11/066,346, filed Feb. 25, 2005, entitled "Minimally-Invasive Cardiac-Valve Prosthesis" and U.S. patent application Ser. No. 11/352,021, filed Feb. 10, 2006, entitled "Cardiac-Valve Prosthesis," both of which are hereby incorporated by reference.

According to the embodiment shown in FIGS. 1 and 3, the legs 60, 62 of the U-shaped portion 66 define a double curvature. The first curve, which is convex with respect to a longitudinal centerline of the valve 2, extends outwardly away from the outflow ring 21 of the anchoring structure 6. This first curve has a radius of curvature, R1, selected such that the legs 60, 62 generally conform to the curvature at the distal portion of the Valsalva sinus. The second curve, which is concave with respect to a longitudinal centerline of the valve 2, has a radius of curvature, R2, selected such that the legs 60, 62 generally conform to the curvature of the proximal portion of the Valsalva sinus.

As will be appreciated by those skilled in the art, the aortic root of the normal heart includes three aortic sinuses, which are distributed in an approximately angularly uniform way around the root of the artery distal to the semi-lunar valve (i.e., the aortic or pulmonary valve). According to various embodiments, as illustrated in FIGS. 2-3, the anchoring structure 6 includes three arms 10 set at an angular distance apart of about 120° with respect to a longitudinal axis of the prosthetic valve 2. According to other embodiments, the prosthetic valve 2 includes more or fewer anchoring arms 10 to match human anatomies includes more or fewer aortic sinuses.

According to various embodiments, the anchoring arms 10 are shaped such that, in the expanded configuration, the arms 10 apply an outwardly directed radial force against an inner wall of the Valsalva sinus. In some embodiments, the arms 10 are configured such that this radial force is selected to sufficiently anchor that prosthetic valve 10 at the Valsalva sinus under operating conditions typically present during the human cardiac cycle.

FIG. 4 is a top cross-sectional view of a prosthetic valve 100 implanted at a native aortic valve site, according to an embodiment of the invention. As shown, and as discussed in detail above, the prosthetic valve 100 can be implanted such that the annular member 152 of the anchoring structure occupies a position distal to the Valsalva sinuses (VS). According to various embodiments, the arms 110 can be arranged and positioned relative to the sinuses of Valsalva such that each of the arms 110 projects into the respective sinus of Valsalva and substantially engages the sinus wall. More particularly, as discussed above, the arms 110 project into the Valsalva sinus and rest in a space defined between an open valve leaflet and the sinus wall. As shown in FIG. 4, each of the arms 110 can be positioned on opposite sides of the coronary ostia (CO) in the respective sinuses of Valsalva. The valve leaflets 24a, 24b, 24c can be positioned within the lumen for blood flow formed by the annular member 152 with the support members (not visible) extending into the lumen by a minimal amount. Upon implantation, the arms 110 of the anchoring structure engage or bear against the walls of the valve sinus at the implantation site, without interfering with the blood flow.

FIG. 5 is a flow chart 200 of a method of implanting an expandable heart valve prosthesis according to an embodiment of the present invention. First, a valve prosthesis including an anchoring structure, is transitioned from an expanded position to a collapsed position adapted for delivery of the prosthesis to an implantation site within a patient's heart (block 210). In various embodiments, the prosthesis is delivered using any of a variety of known minimally-invasive delivery techniques. According to one embodiment, the valve is delivered using an off-pump or beating heart procedure. In some embodiments, a crimping tool or other similar device known to those of skill in the art, can be used to radially collapse the prosthetic heart valve including the anchoring structure. One such crimping system, for example, is disclosed in co-pending, commonly assigned U.S. patent application Ser. No. 11/776,695, filed on Jul. 12, 2007, entitled "Expandable Prosthetic Valve Crimping Device," which is hereby incorporated by reference. After the prosthesis has been transitioned from an expanded position to a collapsed position, the prosthesis can be loaded into a delivery catheter. The prosthesis, according to various embodiments, is delivered using a valve delivery system of the type disclosed in U.S. patent application Ser. No. 11/851, 523, entitled "Prosthetic Valve Delivery System Including Retrograde/Antegrade Approach," and/or U.S. patent application Ser. No. 11/851,528, entitled "Fluid-Filled Prosthetic Valve Delivery System," both filed Sep. 7, 2007, both of which are hereby incorporated by reference.

The prosthesis is then delivered to a target implantation site within a patient's heart using known methods and techniques in a minimally invasive manner (block 220). According to some embodiments, the delivery catheter is withdrawn facilitating the automatic expansion of the prosthesis including the support structure from its collapsed configuration to its expanded configuration (block 230). According to further embodiments, an inflatable balloon can be inserted and expanded within the prosthetic heart valve facilitating expansion of the valve and the support structure.

Once expanded, an annular outflow ring of the prosthetic valve is located generally distal with respect to the valve sinus, and an annular inflow ring is located generally at or near the native valve annulus. In embodiments where the arms are fabricated of a resilient, shape memory material, the arms automatically expand into position such that they generally engage the walls of the valve sinus. The arms, according to various embodiments, engage a space between a native valve leaflet and a sinus wall such that they anchor and secure the prosthesis at the implantation site. In this configuration, the arms generally resist downward movement in response to the pressure exerted upon the prosthesis, such that the valve remains at the desired implantation site (block 240).

Figure 6:
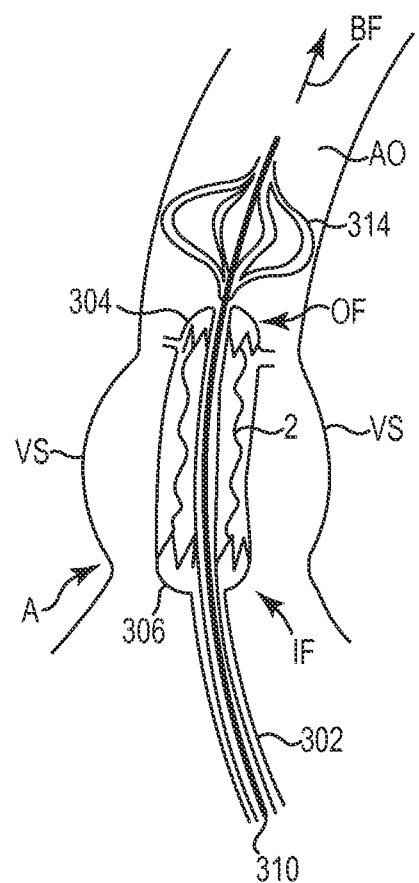
FIG. 6 is a schematic view of a delivery system for implanting an expandable prosthetic valve according to various embodiments of the present invention.

FIG. 6 is a schematic view of a delivery system 300 for delivering the prosthetic valve 2 to the desired implant location. As shown in FIG. 6, the delivery system 300 is being used to introduce the prosthetic valve 2 in the same direction as the blood flow, BF. In other words, as shown in FIG. 6, the delivery system 300 is being introduced into to the Valsava sinus (VS) region of the aortic valve through the left ventricle. As shown, the delivery system 300 includes a sheath or catheter 302, a first deployment element 304, and a second deployment element 306. The prosthetic valve 2 is shown in its collapsed configuration and is disposed inside the deployment elements 304, 306. As further shown in FIG. 6, in various exemplary embodiments, the delivery system 300 includes a guidewire or stylet 310 coupled to a centering mechanism 314. The centering mechanism 314 may be used to help center the delivery system 300 in the aorta (AO) during an implantation procedure. During implantation, the delivery system 300 is used to advance the prosthetic valve to the desired implant location, for example, at or near the annulus (A) of the native aortic valve. Once disposed at the desired location, the implanting physician may activate the deployment elements 304, 306, by causing one or both to move back or forth with respect to the prosthetic valve 2, which thereby releases the valve and allows is to expand radially and contact the wall of the annulus, aorta, and/or valve sinus. According to other embodiments, other delivery systems may be used to implant the prosthetic valve 2. Exemplary delivery systems are disclosed in U.S. patent application Ser. No. 11/612,974, filed Dec. 19, 2006, entitled "System for In Situ Positioning of Cardiac Valve Prostheses Without Occluding Blood Flow," and U.S. patent application Ser. No. 11/612,980, filed Dec. 19, 2006, entitled "Instrument and Method for In Situ Deployment of Cardiac Valve Prostheses," both of which are hereby incorporated by reference.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A valve prosthesis for implantation in or near a human heart at a valve site, the valve site including one or more valve sinuses, the prosthesis having a principal axis extending longitudinally therethrough and comprising:
an anchoring structure comprising an annular outflow member, an annular inflow member, three straight support members connected to and extending between the annular outflow member and the annular inflow member, and three arms with each of the three arms having a first end coupled to the annular outflow member and a second end configured to contact a base of the valve sinus, wherein the three arms are angularly spaced apart from one another about the principal axis of the prosthesis and are immediately adjacent one another, such that each of the three arms is non-overlapping with each immediately adjacent arm and a different one of the three straight support members is positioned between a pair of the immediately adjacent arms; and
three leaflets directly attached to the three straight support members of the anchoring structure and adapted to allow blood flow in a first direction and to prevent blood flow in a second direction;
wherein the annular outflow member has a mesh structure having an expanded position such that in the expanded position the mesh structure is configured to engage a vessel wall at a location distal to the valve sinus, the annular outflow member being distal to the entirety of the three leaflets and wherein at least one of the three arms is shaped to engage at least a portion of a longitudinally extending surface of the valve sinus.

2. The valve prosthesis of claim 1 wherein each of the arms includes a first leg and a second leg and a U-shaped portion extending between the first and second legs.

3. The valve prosthesis of claim 1 wherein the three arms are configured to secure and stabilize the valve prosthesis at an implantation site relative to native heart valve leaflets.

4. The valve prosthesis of claim 1 wherein the three arms are configured to project into a space defined between an open valve leaflet and the sinus wall.

5. The valve prosthesis of claim 1 wherein the three arms comprise a shape memory material.

6. The valve prosthesis of claim 1 wherein the anchoring structure comprises a shape memory material.

7. The valve prosthesis of claim 1 wherein the three arms and said anchoring structure are dimensioned so that a native heart valve leaflet can fit therebetween.

8. The valve prosthesis of claim 1 wherein the annular inflow member is dimensioned to secure the valve prosthesis against a proximal surface of the valve annulus.

9. A valve prosthesis comprising three valve leaflets coupled to an anchoring structure and having a distal end, the anchoring structure including an annular inflow member, an annular outflow member, three straight support members directly connected to and extending between the annular outflow member and the annular inflow member, and three anchoring arms, wherein each of the three anchoring arms is adapted to engage a valve sinus and has an outflow end attached to the annular outflow member, the outflow ends of the three anchoring arms are angularly spaced apart from each other around a principal axis of the prosthesis that extends longitudinally therethrough, each of the three anchoring arms is adjacent two other anchoring arms of the three anchoring arms and non-overlapping with each of the two immediately adjacent other anchoring arms, and each of the three anchoring arms is directly connected to only the annular outflow member and includes a free end adapted to contact a base of the valve sinus adjacent one or more native valve leaflets, wherein the annular outflow member is distal to the distal end of the three valve leaflets.

10. The valve prosthesis of claim 9 further comprising a seal disposed between a proximal end of the anchoring structure and the one or more native valve leaflets.

11. A valve prosthesis for implantation in or near a human heart at a valve site, the valve site including one or more valve sinuses, the prosthesis having a principal axis extending longitudinally therethrough and comprising:
an anchoring structure comprising an annular outflow member, an annular inflow member, three straight support members connected to and extending between the annular outflow member and the annular inflow member, and three arms with each arm of the three arms having outflow ends attached to the annular outflow member at distinct, spaced-apart locations on the annular outflow member and each arm of the three arms configured to contact a base of the one or more valve sinuses, wherein the outflow ends of the three arms are angularly spaced apart from one another about the principal axis of the prosthesis and the three arms are adjacent one another, such that each of the three arms is non-overlapping with an immediately adjacent arm of the three arms and a different one of the three straight support members is positioned between each pair of the immediately adjacent arms; and
three leaflets directly attached to the three straight support members of the anchoring structure, the three leaflets having a distal end and adapted to allow blood flow in a first direction and to prevent blood flow in a second direction;
wherein the annular outflow member has an expanded position configured to engage a vessel wall at a location distal to the valve sinus, the annular outflow member distal to the distal end of the three leaflets and wherein at least one of the three arms is shaped to engage at least a portion of a longitudinally extending surface of the one or more valve sinuses.

12. The valve prosthesis of claim 11 wherein each of the arms includes a first leg coupled to the annular outflow member and a second leg coupled to the annular outflow member and a U-shaped portion extending between the first leg and the second leg.

13. The valve prosthesis of claim 11 wherein the three arms are configured to secure and stabilize the valve prosthesis at an implantation site relative to native heart valve leaflets.

14. The valve prosthesis of claim 11 wherein the three arms are configured to project into a space defined between an open valve leaflet and the sinus wall.

15. The valve prosthesis of claim 11 wherein the three arms comprise a shape memory material.

16. The valve prosthesis of claim 11 wherein the anchoring structure comprises a shape memory material.

17. The valve prosthesis of claim 11 wherein the three arms and said anchoring structure are dimensioned so that a native heart valve leaflet can fit therebetween.

18. The valve prosthesis of claim 11 wherein the annular inflow member is dimensioned to secure the valve prosthesis against a proximal surface of the valve annulus.

* * * * *